United States Patent [19]

Müller et al.

[11] Patent Number: 5,207,577
[45] Date of Patent: May 4, 1993

[54] (METH)ACRYLOYLAMINOALKYL CARBOXYLATES FOR TREATMENT OF COLLAGEN-CONTAINING MATERIALS

[75] Inventors: Michael Müller, Bergisch Gladbach; Wolfgang Podszun, Cologne, both of Fed. Rep. of Germany

[73] Assignee: Bayer Aktiengesellschaft, Leverkusen, Fed. Rep. of Germany

[21] Appl. No.: 646,562

[22] Filed: Jan. 25, 1991

[30] Foreign Application Priority Data

Feb. 6, 1990 [DE] Fed. Rep. of Germany ....... 4003435

[51] Int. Cl.$^5$ ............................................. A61C 6/083
[52] U.S. Cl. ................... 433/217.1; 433/228.1; 523/115; 523/116; 523/118; 522/174; 522/178; 522/14; 522/16; 522/29; 522/37; 522/40; 522/43; 522/66; 522/68; 522/75; 522/84; 526/304
[58] Field of Search ................ 526/304; 523/116, 118, 523/115; 522/174; 433/217.1, 228.1

[56] References Cited

U.S. PATENT DOCUMENTS 3,262,985 7/1966 Müller .............................. 526/304 X
4,698,376 10/1987 Asmussen ............................ 523/115
4,910,268 3/1990 Kobayashi ............................ 525/411

FOREIGN PATENT DOCUMENTS 0051796 5/1982 European Pat. Off. .
0141324 5/1985 European Pat. Off. .
0394792 10/1990 European Pat. Off. .
1123475 2/1962 Fed. Rep. of Germany .
3619914 12/1986 Fed. Rep. of Germany .

*Primary Examiner*—Joseph L. Schofer
*Assistant Examiner*—Mark Nagumo
*Attorney, Agent, or Firm*—Sprung, Horn, Kramer & Woods

[57] ABSTRACT

A dental adhesive comprising a (meth)acryloylaminoalkyl carboxylate of the formula

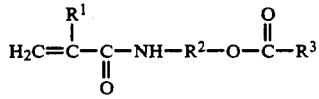

in which
R$^1$ represents hydrogen or methyl;
R$^2$ represents methylene or ethylene; and
R$^3$ represents hydrogen, methyl, or ethyl;

and at least one of an initiator, a non-toxic solvent, and a filler. The dental adhesive is useful to effect a strong adhesive bonding of dental materials to collagen-containing materials.

19 Claims, No Drawings

(METH)ACRYLOYLAMINOALKYL CARBOXYLATES FOR TREATMENT OF COLLAGEN-CONTAINING MATERIALS

The invention relates to preparations for use as an adhesive component for the treatment of collagen-containing materials, and to processes for the preparation and the use of these preparations.

The preparations claimed contain (meth)acryloylaminoalkyl carboxylates (I) of the formula

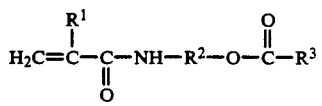

in which
R$^1$ denotes hydrogen or methyl,
R$^2$ denotes methylene or ethylene and
R$^3$ represents hydrogen, methyl or ethyl, and, if desired, additives such as initiators, solvents and fillers.

Collagen-containing materials are albuminoid bodies and principal constituents of the human and animal intercellular supporting substances, such as cartilage and bone tissue, skin and dentine. In the context of the present invention, the adhesive components are preferably used for the treatment of dentine in connection with dental repairs.

Particularly in the dental field, setting polymeric materials are used as filling materials in dental repairs. In general, fillings based on acrylates are preferred as setting polymeric materials. However, these polymeric fillings have the disadvantage that they adhere poorly to the dentine. In order to solve this problem, undercuttings on the dentine have previously sometimes been carried out; for this purpose it was necessary to remove considerable amounts of healthy dentine beyond the affected region.

According to another method, the dentine and the enamel surface are etched with acids, such as, for example, phosphoric acid, and the filling is then performed. Apart from the fact that the acid exerts an irritant action in the oral region, it also penetrates easily into the tooth through the dental tubules and damages the nerve (pulp).

In J. Dent. Res. 57, 500–505 (1978), aldehyde group-containing methacrylates of the isomeric hydroxybenzaldehydes are described which can be used as foundations for fillings in the dental field. However, even after such a foundation, the bond between dentine and filling material remains unsatisfactory.

In Scand. J. Dent. Res. 92, 980–983 (1948) and J. Dent. Res. 63, 1087–1089 (1984), foundations based on aqueous formaldehyde or glutaraldehyde and β-hydroxyethyl methacrylate (HEMA) are described.

In addition, compositions formed from an aldehyde and an olefinically unsaturated monomer containing active hydrogen, which bond to dentine, are described in EP-A-0,141,324.

The new preparations based on (meth)acryloylaminoalkyl carboxylates (I) effect a strong adhesive bonding of materials which are intended to be attached to collagen, for example an adhesive bonding of dental filling material in a cavity in the tooth.

The (meth)acryloylaminoalkyl carboxylates (I) are known synthesis intermediates and were used, for example, as a monomer component for the preparation of copolymers (DE-OS (German Published Specification) 2,217,746, DE-OS (German Published Specification) 1,927,642 and DE-OS (German Published Specification) 3,619,914).

(Meth)acryloylaminomethyl carboxylates were obtained by esterification of N-hydroxymethyl(meth)-acrylamide (DE-OS (German Published Specification) 1,927,642, DE-OS (German Published Specification) 1,281,438). (Meth)acryloylaminomethyl carboxylates can correspondingly be prepared from N-2-hydroxyethyl(meth)-acrylamide (JA 60,262,805).

The good activity of the (meth)acryloylaminoalkyl carboxylates (I) in the preparations according to the invention as an adhesive component for collagen-containing materials was surprising since they do not contain any reactive groups which can form suitable chemical bonds to collagen-containing materials under mild conditions, which was hitherto assumed to be an important requirement (J. C. Sectos, Am. J. Dent. 1. (1988) 173).

For example, the following (meth)acryloylaminoalkyl carboxylates may be mentioned as components of the preparations according to the invention:

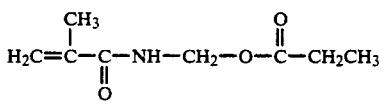

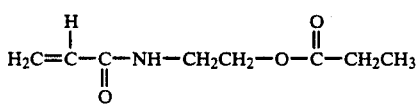

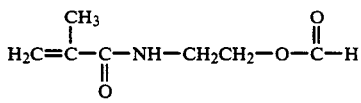

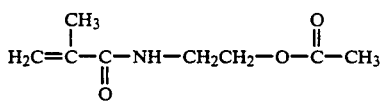

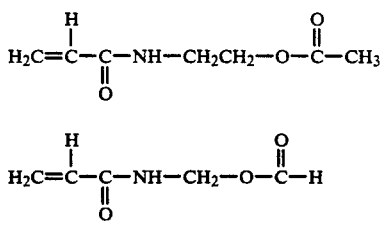

Particularly preferred (meth)acryloylaminomethyl carboxylates are those of the formulae:

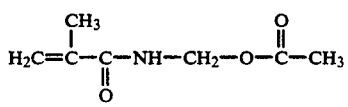

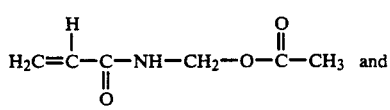 and

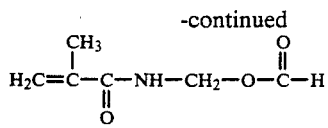

Initiators in the context of the present invention are free radical generators which induce a free radical polymerization. Photoinitiators, which induce a free radical polymerization under the action of light, for example UV light, visible light or laser light, are preferred.

The so-called photopolymerization initiators are known per se (Houben-Weyl, Methoden der organischen Chemie (Methods of Organic Chemistry), Volume E 20, page 80 et seq, Georg Thieme Verlag Stuttgart 1987). Preferably, these are mono- or dicarbonyl compounds, such as benzoin and its derivatives, in particular benzoin methyl ether, benzil and benzil derivatives, for example 4,4-oxydibenzil and other dicarbonyl compounds such as diacetyl, 2,3-pentanedione and α-diketo derivatives of norbornane and substituted norbornanes, metal carbonyls such as manganese pentacarbonyl or quinones such as 9,10-phenanthrenequinone and naphthoquinone. Camphorquinone is particularly preferred.

The preparations according to the invention in general contain 0.01 to 2 parts by weight, preferably 0.1 to 0.5 part by weight of the initiator, relative to 100 parts by weight of polymerizable compounds. If one of the parts to be joined which is in contact with the adhesive component according to the invention already contains an initiator of the type described, the initiator in the adhesive component can even be completely dispensed with.

The solvents in the context of the present invention should dissolve the component and, because of the application, should be non-toxic. Water and volatile organic solvents such as methanol, ethanol, propanol, isopropanol, acetone, methyl ethyl ketone, methyl acetate or ethyl acetate and tetrahydrofuran may be mentioned as preferred.

In general, 10 to 1000 percent by weight, preferably 50 to 300 percent by weight, of the solvent are employed, relative to the (meth)acryloylaminoalkyl carboxylate.

It may be advantageous to add coactivators, which accelerate the polymerization reaction, to the preparations according to the invention. Known accelerators are, for example, amines such as p-toluidine, dimethyl-p-toluidine, trialkylamines such as trihexylamine, polyamines such as N,N,N',N'-tetraalkylalkylenediamine, barbituric acid and dialkylbarbituric acid.

The coactivators are in general employed in an amount from 0.02 to 4% by weight, preferably 0.2 to 1% by weight, relative to the amount of polymerizable compounds.

The compositions according to the invention may contain carbonyl compounds as a further component.

Carbonyl compounds in the context of the present invention are aldehydes and ketones which contain 1 to 20, preferably 1 to 10, and particularly preferably 2 to 6, carbon atoms. The carbonyl function can be bonded to an aliphatic, aromatic or heterocyclic molecule moiety.

Aldehydes which may be mentioned are aliphatic mono- or dialdehydes. Formaldehyde, acetaldehyde, propionaldehyde, 2-methylpropionaldehyde, butyraldehyde, benzaldehyde, vanillin, furfural, anisaldehyde, salicylaldehyde, glyoxal, glutaraldehyde and phthalaldehyde are preferred. Glutaraldehyde is particularly preferred.

Ketones which may be particularly mentioned are aliphatic mono- and diketones. Butanone, acetone, cyclooctanone, cycloheptanone, cyclohexanone, cyclopentanone, acetophenone, benzophenone, 1-phenyl-2-propanone, 1,3-diphenyl-2-propanone, acetylacetone, 1,2-cyclohexane-dione, 1,2-cyclopentanedione and camphorquinone are preferred. Cyclopentanone is particularly preferred.

In general, 1 to 1000 percent by weight, preferably 5 to 50 percent by weight of the carbonyl compounds are employed, relative to the (meth)acryloylaminoalkyl carboxylate.

As a further component, the compositions according to the invention can contain (meth)acrylic acid esters which can form cross-linkages. (Meth)acrylic acid esters which can form cross-linkages in general contain 2 or more polymerizable active groups in the molecule. Esters of (meth)acrylic acid with dihydric to pentahydric alcohols containing 2 to 30 carbon atoms may be mentioned as preferred. Alkoxy(meth)acrylates and urethane group-containing (meth)acrylates are particularly preferred.

(Meth)acrylic acid esters of the formula

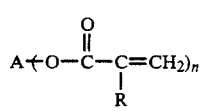

in which

A denotes a straight-chain, branched, cyclic, aliphatic, aromatic or mixed aliphatic-aromatic radical having 2° to 25° C. atoms, which can be interrupted by —O—, NH—or O—CO—NH—bridges and can be substituted by hydroxyl, oxy, carboxyl, amino or halogen, R denotes H or methyl and n represents an integer from 2 to 8, preferably 2 to 4, may be mentioned as examples.

Compounds of the following formulae:

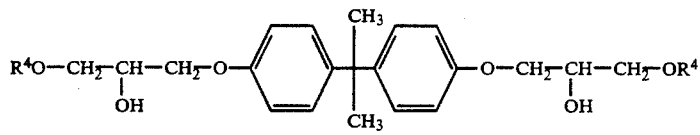

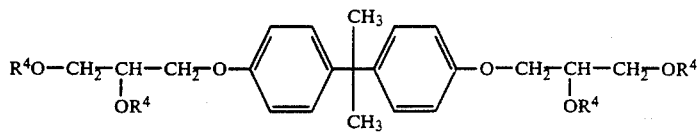

-continued
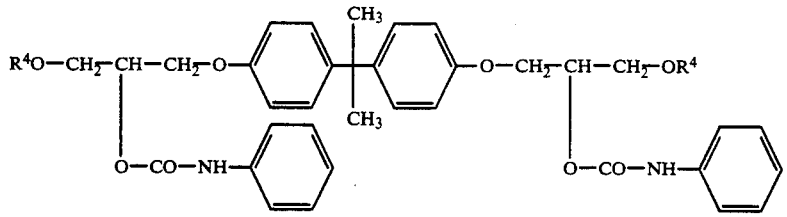
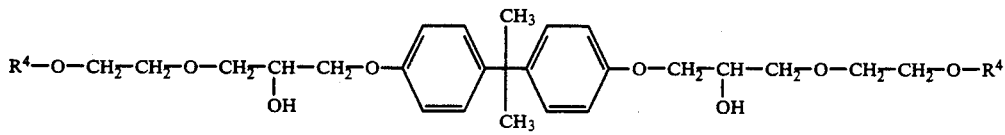
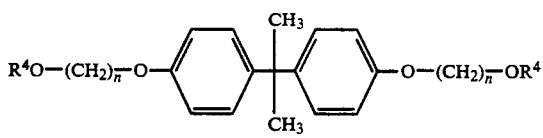
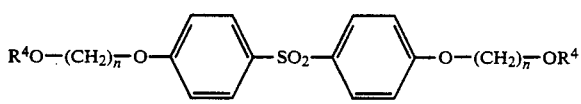
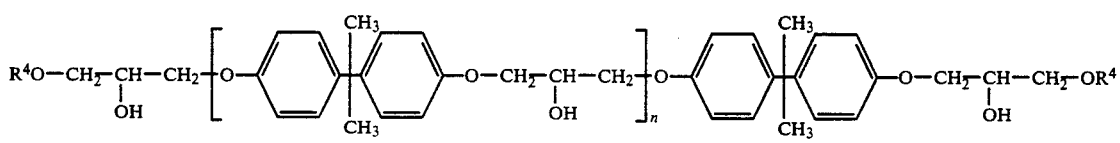
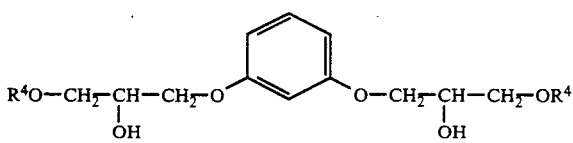
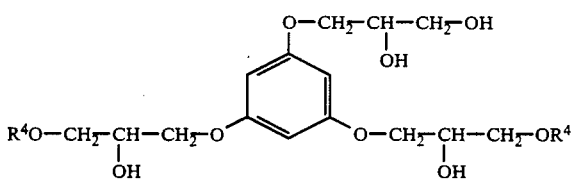
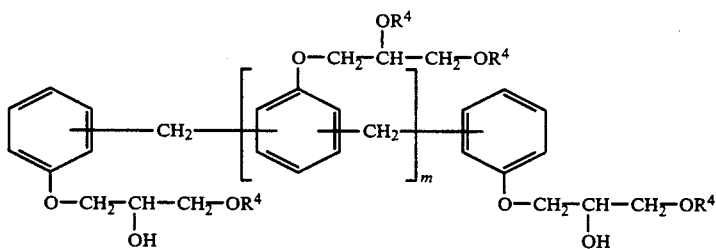
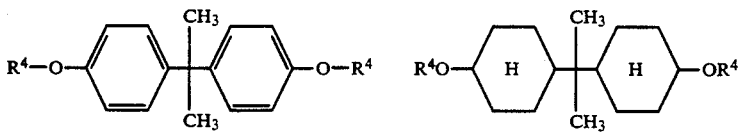
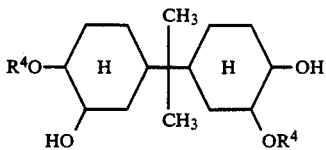

-continued
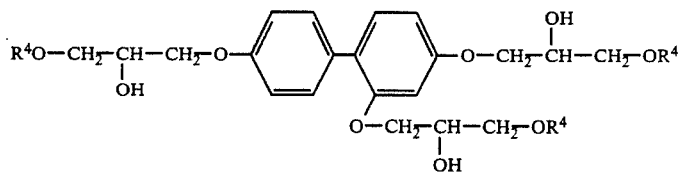
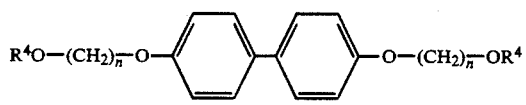
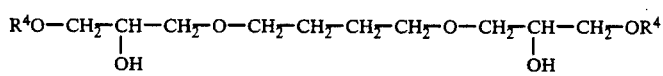
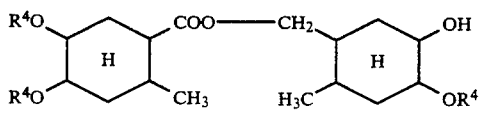
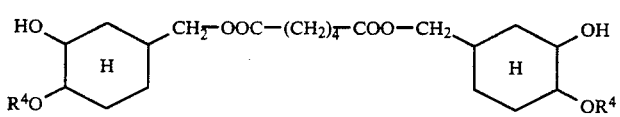
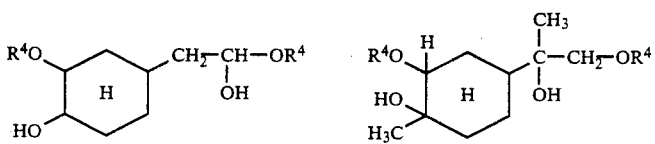
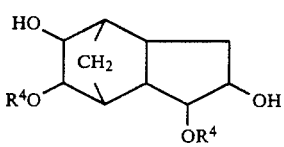
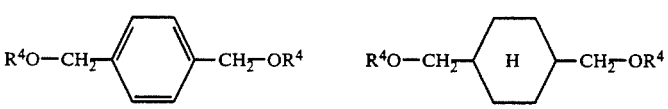
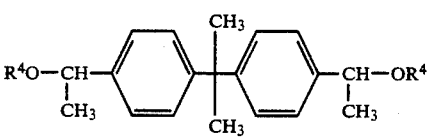
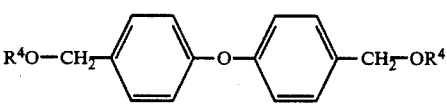
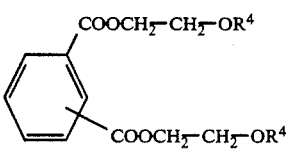
in the ortho-, meta- or para-form

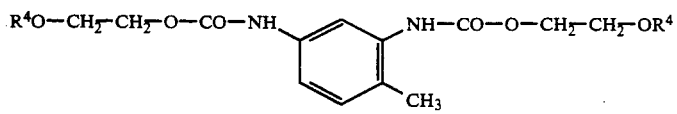
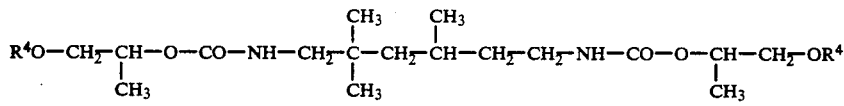
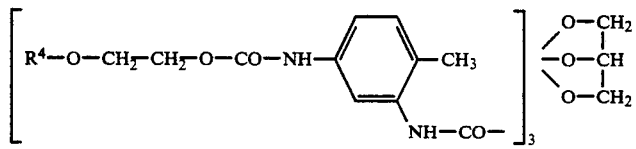
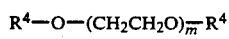
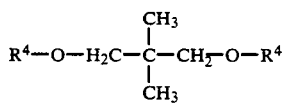
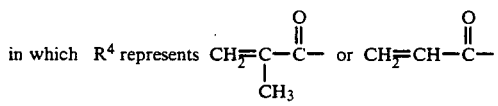
n denotes a number from 1 to 4 and
m denotes a number from 0 to 5, may be mentioned as preferred.
In addition, derivatives of tricyclodecane (EP-A-0,023,686) and reaction products of polyols, diisocyanates and hydroxyalkyl methacrylates (DE-A-3,703,120, DE-A-3,703,080 and DE-A-3,703,130) may be mentioned. The following monomers may be mentioned as examples:
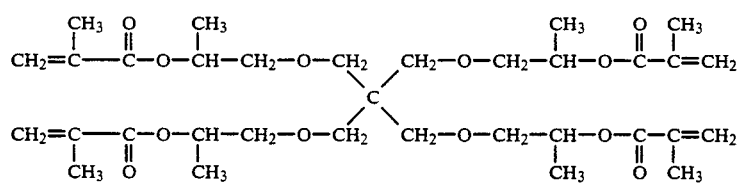
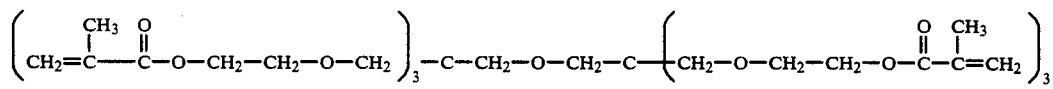
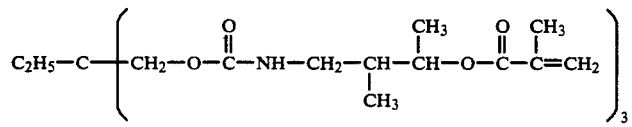
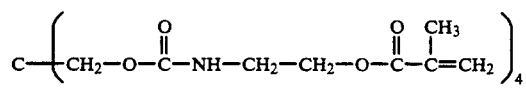
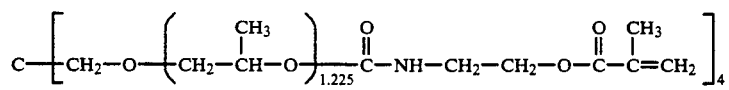

-continued
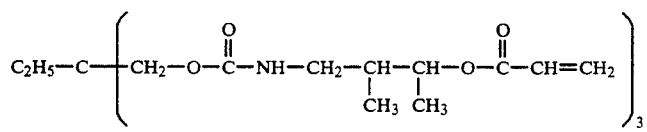
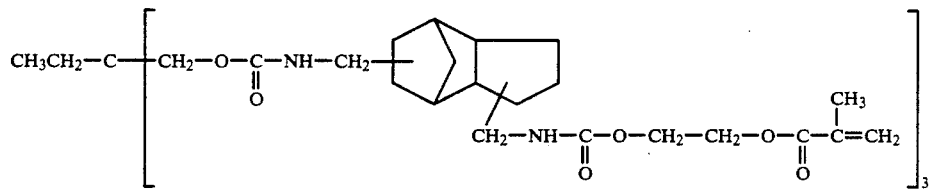
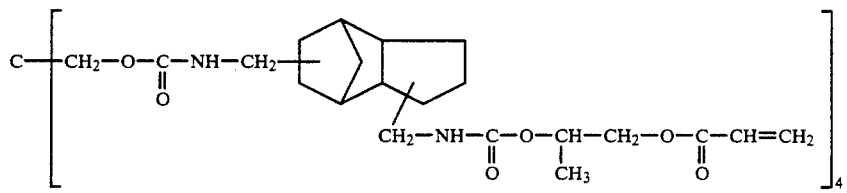
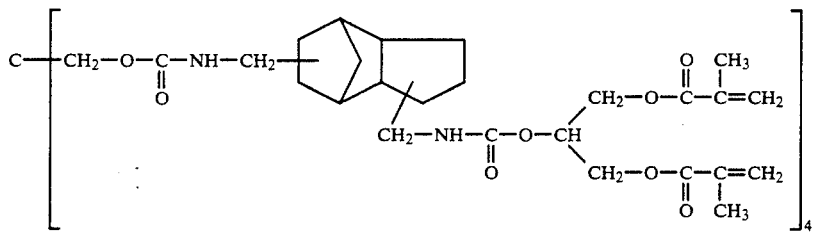
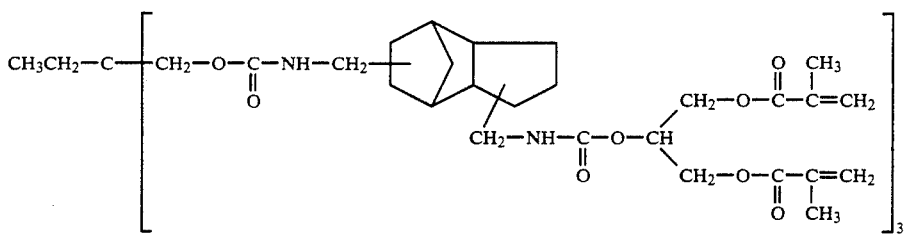
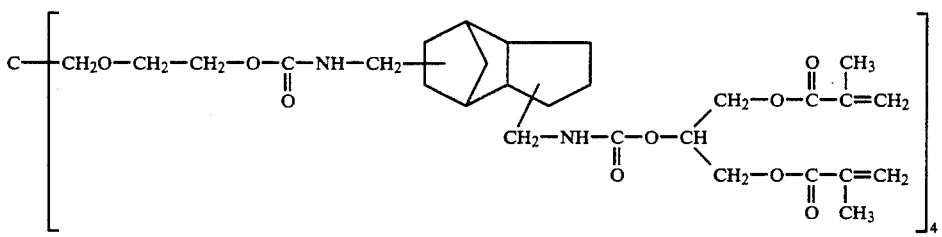
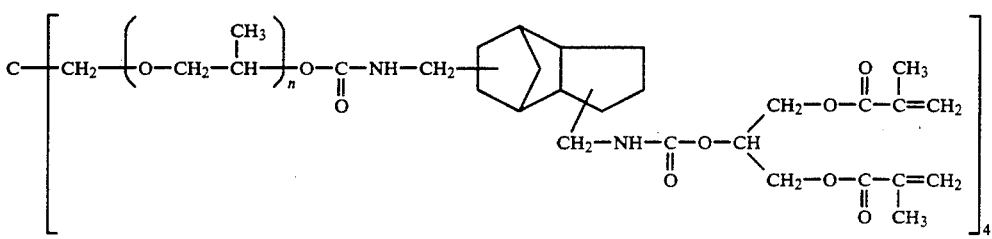
n - 1.225 (statistical mean for 4 chains)

-continued
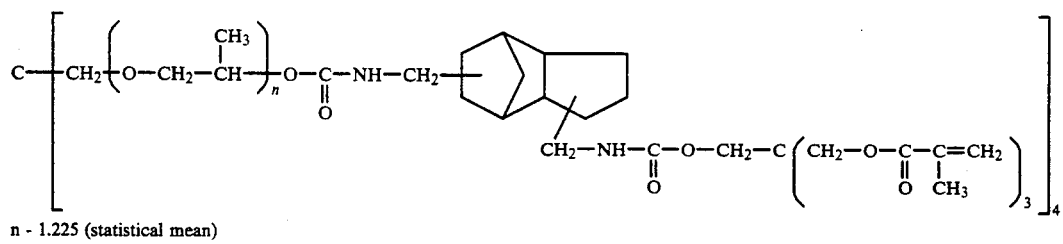
n - 1.225 (statistical mean)
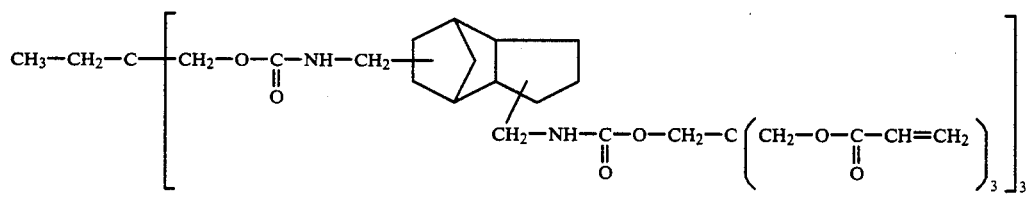
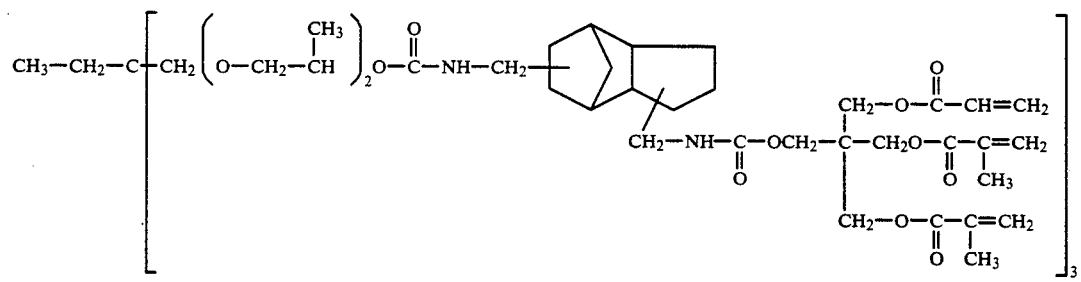
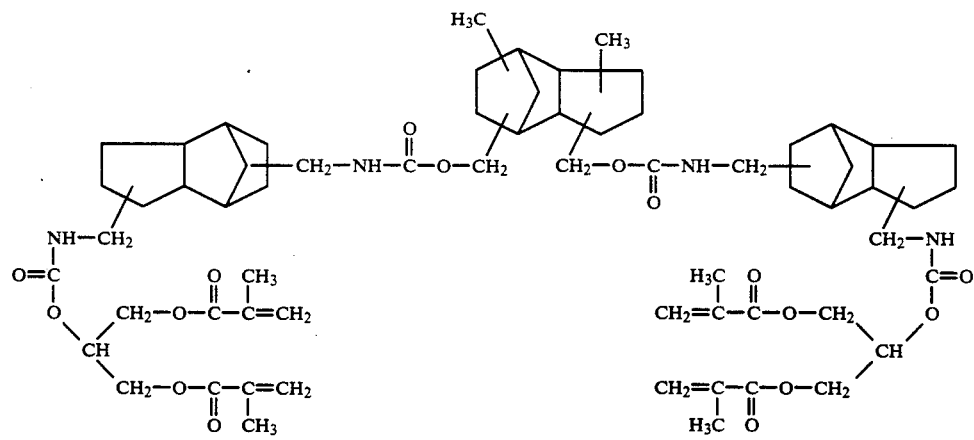
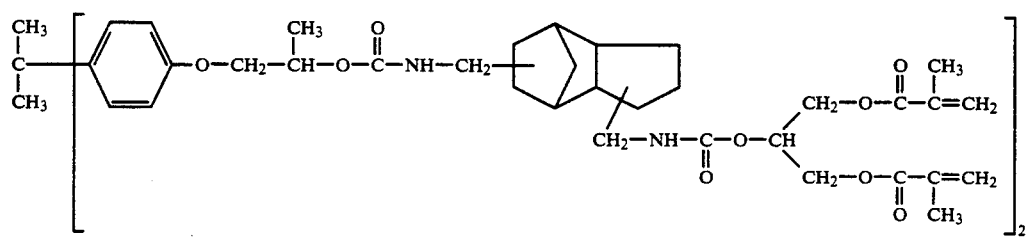

-continued
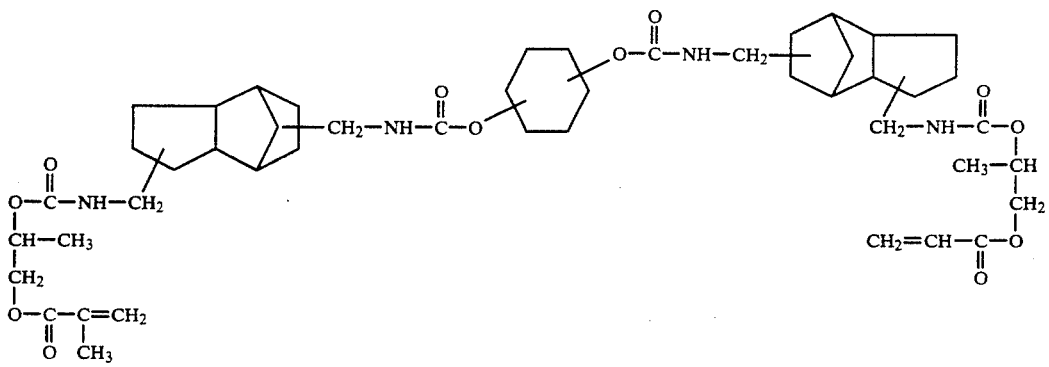
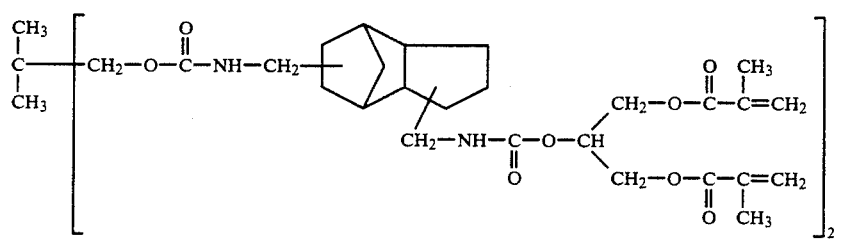
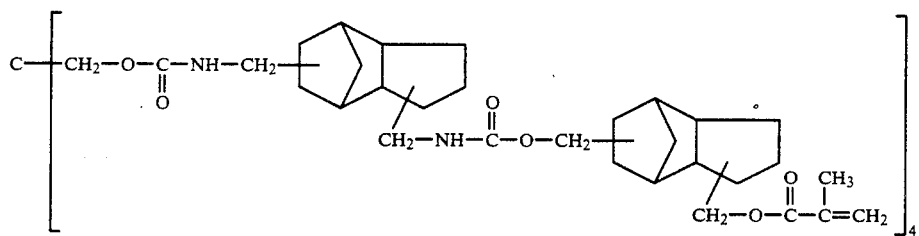
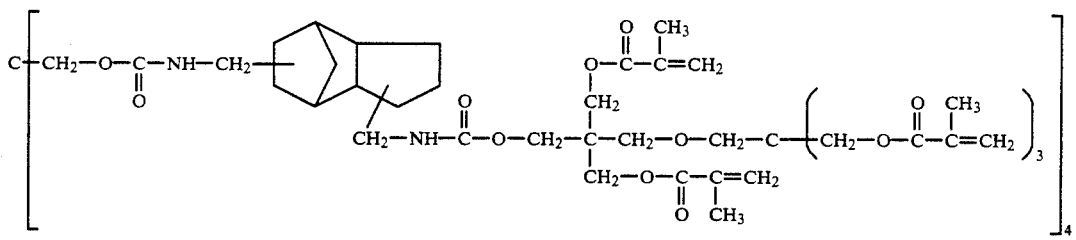
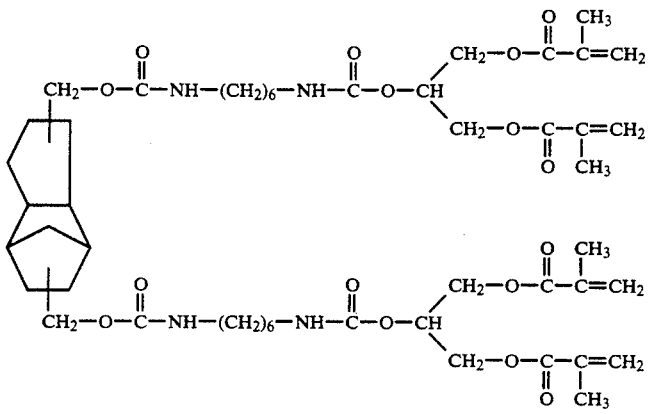

-continued
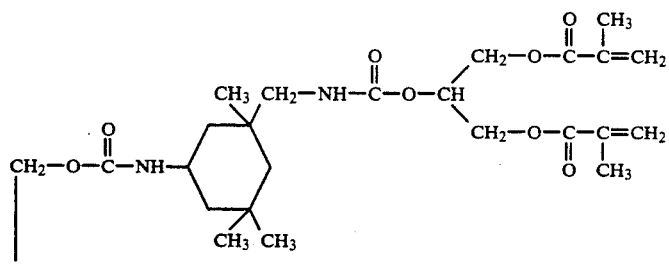
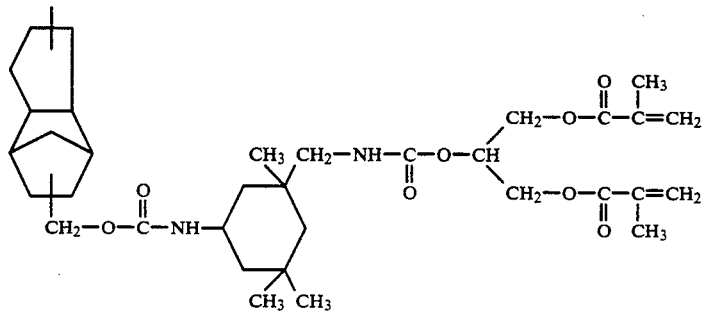
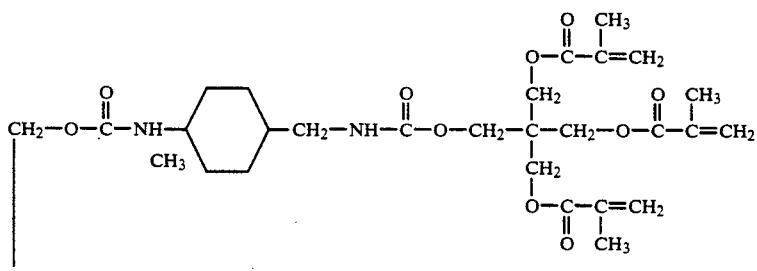
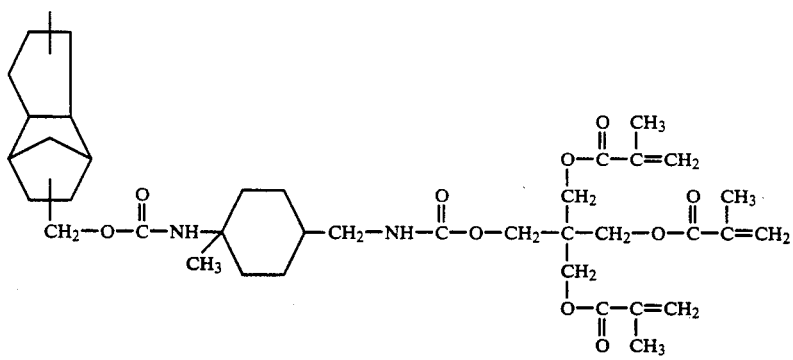
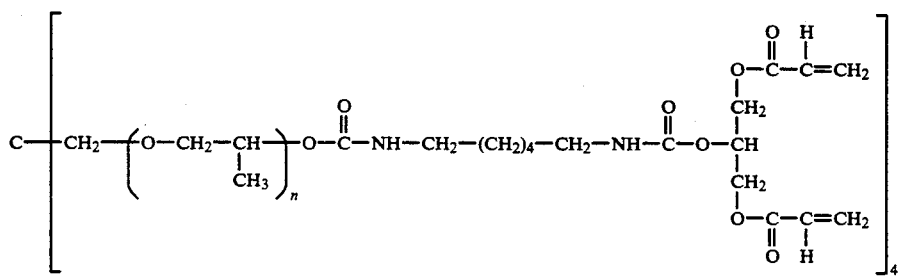
n - 1.225 (statistical mean for 4 chains)

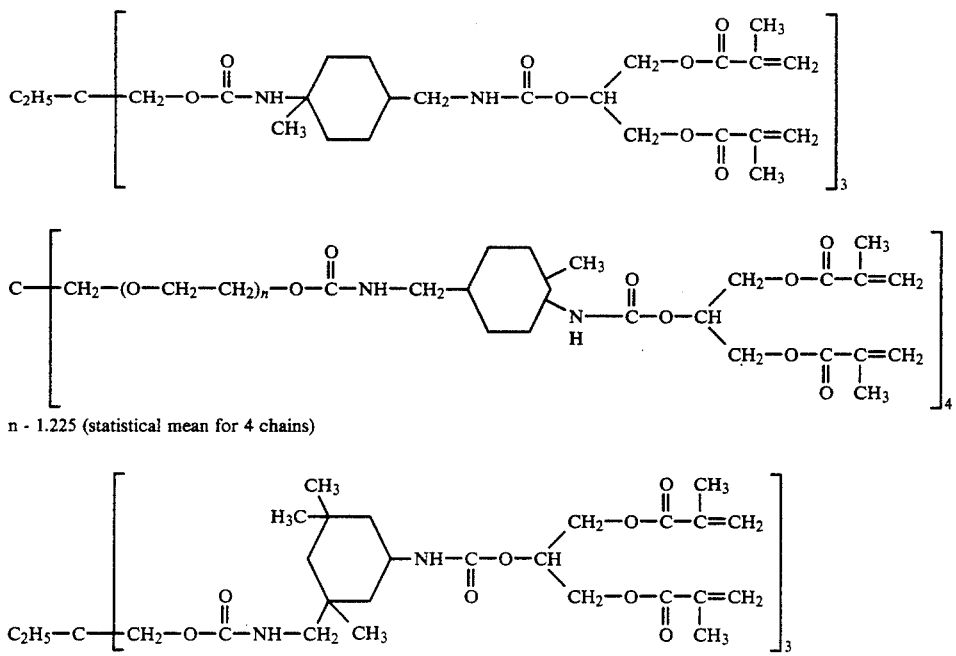

n - 1.225 (statistical mean for 4 chains)

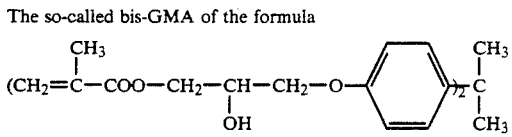

The so-called bis-GMA of the formula

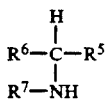

is particularly preferred as a monomer.

Of course, it is possible to employ mixtures of the various (meth)acrylic acid esters which can form crosslinkages. Mixtures of 20 to 70 parts by weight of bis-GMA and 30 to 80 parts by weight of triethylene glycol dimethacrylate may be mentioned as examples.

The preparations according to the invention in general contain 5 to 80percent by weight, preferably 10 to 60 percent by weight, of carboxyl compounds relative to the (meth)acryloylaminoalkyl carboxylate.

The compositions according to the invention may contain fillers as a further component. Fine powders which have a particle diameter in the range from 0.1 to 100 μm (if appropriate also in a polydisperse distribution) are preferred as fillers. Fillers may be fillers customary in the dental field (R. S. Baratz, J. Biomat. Applications, Vol 1, 1987, p 316 et seq.) such as inorganic glasses, silica, alumina or quartz powder.

As a result of a proportion of fillers in the preparations according to the invention, adhesive cements result which are particularly suitable for fixing bridges, crowns and other facing materials.

The proportion of the filler is in general 20 to 80 percent by weight, preferably 40 to 70percent by weight, relative to the total preparation.

The adhesive components according to this invention may furthermore contain up to 10 percent by weight of customary additives such as stabilizers, inhibitors, light-screens, colorants, pigments or fluorescent substances.

The preparations according to the invention can be prepared by mixing the (meth)acryloylaminoalkyl carboxylate and the initiator and, if appropriate, the other components by vigorous stirring.

The preparations may also be solvent-free.

The preparations according to the invention can be used as an adhesive component for the treatment of collagen-containing materials.

In a particular embodiment, the collagen-containing material is conditioned before the treatment with the preparation according to the invention using a liquid having a pH value in the range from 0.1 to 3.5.

This liquid in general contains acids having a pK value of less than 5 and, if appropriate, an amphoteric amino compound having a pK value in the range from 9.0 to 10.6 and a $pK_B$ value in the range from 11.5 to 12.5. The conditioning liquid may contain, for example, the following acids: phosphoric acid, nitric acid, pyruvic acid, citric acid, oxalic acid, ethylenediaminetetraacetic acid, acetic acid, tartaric acid, malic acid and maleic acid.

Amphoteric amino compounds which may be mentioned are preferably compounds of the formula $$R^6-\underset{\underset{R^7-NH}{|}}{\overset{\overset{H}{|}}{C}}-R^5$$

in which $R^5$ represents a carboxyl group, $R^6$ denotes hydrogen or a lower alkyl radical optionally substituted by hydroxyl, thio, methylthio, carboxyl, amino, phenyl, hydroxy-phenyl or the groups

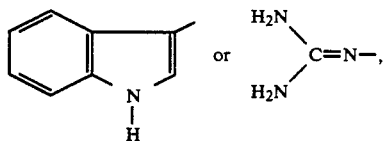

R[7] denotes hydrogen or phenyl, where the radicals R[5] and R[7] can be linked via a propyl radical, or in which R[5] represents hydrogen, R[6] represents the group —B—NH$_3$X, in which B represents a doubly bonded alkylene radical having 1 to 6 carbon atoms and X represents halogen, and R[7] denotes hydrogen.

The following amphoteric amino compounds may be mentioned as examples: glycine, serine, threonine, cysteine, tyrosine, asparagine, glutamine, alanine, valine, leucine, isoleucine, proline, methionine, phenylalanine, tryptophan, lysine, arginine, histidine, N-phenylglycine, ethylenediamine hydrochloride, ethylenediamine hydrobromide, propylenediamine hydrochloride, propylenediamine hydrobromide, butylenediamine hydrochloride, butylenediamine hydrobromide, leucine hydrochloride and histidine hydrochloride.

The conditioning liquid may furthermore contain substances from the group comprising the polyethylene glycols and metal hydroxides. In particular, the above-mentioned polybasic acids can also be employed partly as metal salts as long as free acid functions remain.

Conditioning liquids which contain at least one of the acids from the group comprising pyruvic acid, ethylenediaminetetraacetic acid and citric acid and, if appropriate, an amphoteric amino compound from the group comprising glycine, N-phenylglycine and proline, are particularly preferred.

The application of the preparations according to the invention can be carried out, for example, as follows:

In a dental repair, for example, after a mechanical cleaning of the collagen-containing dental material, the conditioning fluid is first applied using some cotton wool and allowed to act for a short time (for example 60 seconds), and the dental material is rinsed with water and dried in a stream of air. The preparation according to the invention is then applied in a thin layer, for example using a small brush, and dried in a stream of air. After the treatment according to the invention, the actual filling material, for example plastic filling materials customary in the dental field (K. Eichner, "Zahnärztliche Werkstoffe und ihre Verarbeitung" (Dental materials and their processing), Vol. 2, p. 135 et seq, Hüthig Verlag, 5th Edition 1985) is applied.

In a similar fashion, the preparations according to the invention can be used for fixing crowns, bridges and similar aids.

EXAMPLES 1 TO 3 (PREPARATION)

The adhesives according to the invention are produced by intensive mixing of the components shown in the following examples.

| Example 1 | 46 g | of methacryloylaminomethyl acetate |

| | | of the formula |
| | | 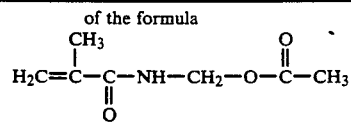 |
| | 54 g | of water |
| | 125 mg | of camphorquinone |
| Example 2 | 40 g | of methacryloylaminomethyl acetate |
| | 42 g | of water |
| | 18 g | of 25% strength by weight aqueous glutaraldehyde solution |
| | 125 mg | of camphorquinone |
| Example 3 | 35 g | of methacryloylaminomethyl propionate of the formula |
| | | 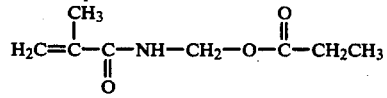 |
| | 35 g | of water |
| | 20 g | of 25% strength by weight aqueous glutaraldehyde solution |
| | 10 g | of tetrahydrofuran |
| | 125 mg | of camphorquinone |

EXAMPLE 4 (USE)

The suitability of the adhesives corresponding to Examples 1 to 3 is tested by determining the tensile binding strength of the light-activated plastic filling material based on multifunctional methacrylic acid esters and barium aluminosilicate LUMIFOR ® Light Curing Composite Universal (U) (a resin based light curing hybrid composite for dental application available from Bayer Aktiengesellschaft, a corporation of Germany) to dentine.

Extracted human teeth which had been stored in 1% chloramine solution for no longer than 3 months after extraction were used for the trials. After these teeth had been carefully cleaned under running water, the preparation as far as embedding in epoxy resin (Lekutherm X 257), an epoxy casting resin based on Bisphenol-A and also available from Bayer Aktiengesellschaft, a corporation of Germany was carried out in physiological saline solution.

Using abrasive paper of differing grain sizes, the tooth is ground wet until a sufficiently large dentine surface for bonding a plastic filling material cylinder of φ 3.5 mm is exposed. The exposed dentine surface was finally prepared using silicon carbide paper 600 in the wet.

The dentine is successively pretreated with the EDTA conditioning liquid GLUMA ® Cleanser (60 seconds cleaning with a cotton wool pad, rinsing with water and drying in air) and the adhesive (60 seconds time of action and drying in air).

In order to prepare the sample body for the tensile binding test, the dentine sample prepared as described is tensioned in a stand having a cylindrical divisible TEFLON ®, a trademark for polytetrafluoroethylene, mold. This TEFLON ® mold, altogether 5 mm high, is conically shaped in the upper half so that a tensile test can be carried out using a correspondingly shaped adapter.

A sealing material based on multifunctional methacrylic acid ester BAYER RESIN L ® is applied to the pretreated dentine surface in a thin layer using a brush and additionally distributed using a stream of air.

The sealing material is first irradiated at a distance of 5 mm to the dentine surface using a polymerization light (Translux CL, Kulzer). Incremental mold filling and light activation of the plastic filling material is then carried out.

The light activation time for the plastic filling material is set at a total of 160 seconds owing to the large volume.

After termination of the light activation, the sample body is removed and stored in a water bath at 23° C. until the tensile test.

The tensile bonding strength, the force on fracture of the sample divided by the contact area to the dentine, was measured using a rate of advance of 1 mm/min.

The fracture surface on the dentine is then checked by light microscopy to evaluate the cause of failure. In this connection, cohesive fractures were frequently to be observed, i.e. the bondings produced using the adhesive components according to the invention were stronger than the bonded parts to be joined themselves. This shows the good efficiency of the adhesive components according to the invention.

It will be understood that the specification and examples are illustrative but not limitative of the present invention and that other embodiments within the spirit and scope of the invention will suggest themselves to those skilled in the art.

What is claimed is:

1. A dental adhesive consisting of the following ingredients:
   (1) at least one (meth)acryloylaminoalkyl carboxylate of the formula:

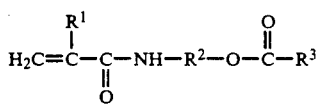

in which
   $R^1$ represents hydrogen or methyl;
   $R^2$ represents methylene or ethylene; and
   $R^3$ represents hydrogen, methyl or ethyl;
   and at least one of the following ingredients:
   (2) about 0.01 to 2 parts by weight initiator relative to 100 parts by weight of polymerizable compounds in the dental adhesive;
   (3) a non-toxic solvent; or
   (4) a filler;
   and optionally at least one of the following ingredients:
   (5) a polymerization reaction accelerator;
   (6) a cross-linkable (meth)acrylic acid ester compound containing two or more polymerizable (meth)acryl groups; or
   (7) an aliphatic mono- or dialdehyde.

2. A dental adhesive according to claim 1, in which
   $R^1$ denotes hydrogen or methyl,
   $R^2$ denotes methylene, and
   $R^3$ represents hydrogen or methyl.

3. A dental adhesive according to claim 1, wherein the (meth)acryloylaminoalkyl carboxylate and the initiator are dissolved in a non-toxic solvent.

4. A dental adhesive according to claim 3, wherein the non-toxic solvent is selected from the group consisting of water, methanol, ethanol, propanol, isopropanol, acetone, methyl ethyl ketone, methyl acetate, ethyl acetate, and tetrahydrofuran.

5. A dental adhesive according to claim 1, including a polymerization reaction accelerator.

6. A dental adhesive according to claim 5, wherein the polymerization reaction accelerator is selected from the group consisting of p-toluidine, dimethyl-p-toluidine, trihexylamine, N,N,N',N'-tetraalkylalkylenediamine, barbituric acid, and dialkylbarbituric acid.

7. A dental adhesive according to claim 1, further containing a cross-linkable (meth)acrylic acid ester compound containing two or more polymerizable (meth)acryl groups.

8. A dental adhesive according to claim 7, wherein the cross-linkable (meth)acrylic acid ester containing two or more polymerizable (meth)acryl groups is selected from the group consisting of (meth)acrylic acid esters of the formula:

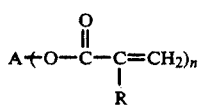

in which
A represents an aliphatic or mixed aliphatic-aromatic radical, having 2–25 carbon atoms, which is uninterrupted or interrupted by —O—, —NH—, or —O—CO—NH—bridges and which is unsubstituted or substituted by hydroxyl, oxy, carboxyl, amino or halogen, or represents aromatic, which is unsubstituted or substituted by hydroxyl, oxy, carboxyl, amino or halogen;
R represents hydrogen or methyl; and
n represents an integer from 2 to 8.

9. A dental adhesive according to claim 1, containing a filler.

10. A dental adhesive according to claim 9, wherein the filler is selected from the group consisting of inorganic glasses, silica, alumina or quartz powder.

11. A dental adhesive according to claim 1, wherein the initiator is present in the dental adhesive in an amount of 0.01 to 2 parts by weight relative to 100 parts by weight of polymerizable compounds in the dental adhesive and the initiator is selected from the group consisting of benzoin, benzoin methyl ether, benzil, 4,4-oxydibenzil, diacetyl, 2,3-pentanedione, manganese pentacarbonyl, 9,10-phenanthrenequinone, naphthoquinone, and camphorquinone.

12. A dental adhesive according to claim 11, wherein the initiator is present in the dental adhesive in an amount of 0.1 to 0.5 parts by weight relative to 100 parts by weight of polymerizable compounds in the dental adhesive.

13. A dental adhesive according to claim 11, wherein the initiator is camphorquinone.

14. A dental adhesive according to claim 1, which contains a mono- or dialdehyde selected from the group consisting of formaldehyde, acetaldehyde, propionaldehyde, 2-methylpropionaldehyde, butyraldehyde, benzaldehyde, vanillin, furfural, anisaldehyde, salicylaldehyde, glyoxal, glutaraldehyde, and phthaldehyde.

15. In the application of an adhesive material to a collagen-containing material, the improvement wherein said adhesive material comprises a (meth)acryloylaminoalkyl carboxylate of the formula

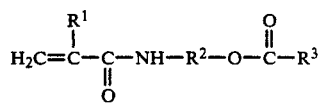 (I)

in which
R¹ denotes hydrogen or methyl,
R² denotes methylene or ethylene and
R³ represents hydrogen, methyl or ethyl.

16. The process according to claim 15, in which
R¹ denotes hydrogen or methyl,
R² denotes methylene, and
R³ represents hydrogen or methyl.

17. The process according to claim 15, wherein the collagen-containing material is a tooth.

18. The process according to claim 15, wherein the collagen-containing material is a bone.

19. The process according to claim 15, wherein the collagen-containing material is pre-treated with a liquid having a pH of about 0.1 to 3.5

* * * * *